(12) United States Patent
Sarkar et al.

(10) Patent No.: US 12,264,117 B2
(45) Date of Patent: Apr. 1, 2025

(54) CATALYTIC PROCESS FOR THE PRODUCTION OF AROMATIC HYDROCARBONS FROM USED COOKING OIL

(71) Applicant: COUNCIL OF SCIENTIFIC AND INDUSTRIAL RESEARCH AN INDIAN REGISTERED BODY INCORPORATED, Delhi (IN)

(72) Inventors: Bipul Sarkar, Uttarakhand (IN); Om Vir Singh, Uttarakhand (IN); Ankit Agrawal, Uttarakhand (IN); Anjan Ray, Uttarakhand (IN); Sanat Kumar, Uttarakhand (IN); Bhanu Prasad Vempatapu, Uttarakhand (IN); Jagdish Kumar, Uttarakhand (IN)

(73) Assignee: COUNCIL OF SCIENTIFIC AND INDUSTRIAL RESEARCH AN INDIAN REGISTERED BODY INCORPORATED UNDER THE REGN. OF SOC. ACT (ACT XXI OF 1860), New Delhi (IN)

( * ) Notice: Subject to any disclaimer, the term of this patent is extended or adjusted under 35 U.S.C. 154(b) by 71 days.

(21) Appl. No.: 18/355,160

(22) Filed: Jul. 19, 2023

(65) Prior Publication Data
US 2024/0025820 A1 Jan. 25, 2024

(30) Foreign Application Priority Data
Jul. 21, 2022 (IN) .............................. 202211041939

(51) Int. Cl.
C07C 1/20 (2006.01)
B01J 37/03 (2006.01)
B01J 37/08 (2006.01)
C07C 1/207 (2006.01)

(52) U.S. Cl.
CPC ........... *C07C 1/2078* (2013.01); *B01J 37/035* (2013.01); *B01J 37/086* (2013.01); *C07C 2529/40* (2013.01); *C07C 2529/46* (2013.01)

(58) Field of Classification Search
CPC .............. C07C 1/2078; C07C 2529/40; C07C 2529/46; C07C 2529/48; B01J 37/035; B01J 37/086; B01J 2229/186; B01J 2235/15; B01J 29/405; B01J 29/46; B01J 29/48
See application file for complete search history.

(56) References Cited

U.S. PATENT DOCUMENTS

| 2007/0007176 A1 | 1/2007 | Pinho et al. |
| 2018/0010052 A1 | 1/2018 | Sinha et al. |

FOREIGN PATENT DOCUMENTS

| CN | 101314748 A | 12/2008 |
| CN | 101684056 A | 3/2010 |
| CN | 108484346 A | 9/2018 |
| CN | 110694673 A | 1/2020 |
| EP | 2781497 A1 | 9/2014 |
| JP | 2015189712 A | 11/2015 |
| RU | 2652986 C1 | 5/2018 |
| SU | 1714836 A1 | 10/1995 |
| WO | WO-0021661 A1 | 4/2000 |
| WO | WO-2011045482 A1 | 4/2011 |
| WO | WO-2015134570 A1 | 9/2015 |

*Primary Examiner* — Thuan D Dang
(74) *Attorney, Agent, or Firm* — Schwegman Lundberg & Woessner, P.A.

(57) ABSTRACT

The present invention is related to a process for the conversion of used cooking oil into aromatics (BTEX) hydrocarbon as petrochemical building blocks. The process provides an aromatic rich hydrocarbon from used cooking oil in the presence and absence of steam/hydrogen over supported bimetallic alumina-silicates zeolites. The catalyst contains no precious metal entities and may contain one metal form zinc (Zn), a second metal (X), comprising at least one selected from cobalt (Co), gallium (Ga), chromium (Cr), Iron (Fe) and third elements from cerium (Ce), boron (B) supported on alumina-silicates zeolites. The present invention relates to a catalyst excluding novel metals to produce aromatics in a continuous fixed bed reactor system under atmospheric pressure. More particularly, the present invention relates to a low-temperature process to produce aromatic over alumina-silicates zeolites. The process provides used cooking oil conversion of 84-89% with aromatic selectivity of 87-91%.

4 Claims, 3 Drawing Sheets

CATALYTIC PROCESS FOR THE PRODUCTION OF AROMATIC HYDROCARBONS FROM USED COOKING OIL

CROSS-REFERENCE TO RELATED APPLICATIONS

This Non-provisional application claims priority under 35 U.S.C. § 119(a) to India Patent Application No. 202211041939, filed on 21 Jul. 2022, the entire contents of which is hereby incorporated by reference in its entirety.

FIELD OF THE INVENTION

The present invention relates to a process for converting used cooking oil (UCO) into aromatic (BTEX) rich hydrocarbons useful as petrochemical building blocks. In particular, the present invention relates to a catalyst excluding new Group II-B metals to produce aromatics in a fixed bed continuous reactor system under atmospheric pressure. More particularly, the present invention relates to a low-temperature process for preparing aromatic over alumina silicate zeolites. The process of the present invention relates to low-temperature production of aromatic hydrocarbon (BTX) using supported polymetallic alumina-silicate zeolites MFI. The catalyst may contain zinc (Zn), and a second metal, comprising at least one from cobalt (Co), gallium (Ga), chromium (Cr), iron (Fe) and third elements from cerium (Ce), and boron (B). In contrast, UCO can be potential alternatives that can be used to produce renewable aromatics. The claimed process gives good conversion and aromatics selectivity at low temperature. The material is cost-effective as it doesn't incorporate the precious metals like Platinum (Pt). The developed process finds immense application in the chemical sector.

BACKGROUND OF THE INVENTION

Aromatisation reaction involves dehydrogenation step, an endothermic reaction that requires high temperature and moderate pressure to obtain a high aromatics yield. However, high temperature favours the high yield but leads to the high coke deposition on the catalyst surface, causing rapid catalyst deactivation. Many efforts have been made to maintain the stability, activity and other essential aspects. Technologies like Methaforming (2019) from New Gas Technologies, Aroforming (1991) from IFP and SALUTEC, Z-forming (1992) from Mitsubishi, M-2 forming (1991) from Mobil, and Cyclar (1991) has commercially offered catalyst and process solutions for the continuous production of aromatics from liquid petroleum gas (LPG) and Naphtha based feedstock. The traditional catalysts employed supported or pure zeolite (MFI or FAU). The increasing concerns for environment-friendly sustainability have made it essential to find alternative routes to produce chemicals with biodegradability, renewability, and less dependence on petroleum products. In contrast, used cooking oil (UCO) can be potential alternatives that can be used to produce renewable aromatics. Currently, UCO is being used to produce bio aviation fuel/biodiesel through hydro-processing. The processed fuel can serve as the blend stock for aviation fuel after further cracking and isomerisation. It is stated that sustainable aviation fuels can reduce the industry's carbon footprint by 34 percent. However, to use biofuels in transportation vehicles, the agencies need to ensure the biofuel is of good quality. Given the current demand for petrochemicals, especially aromatics, the UCO can be rerouted for petrochemical production. Since petrochemicals are experiencing a higher price trend than transportation fuels, the demand for aromatics may drive this alternate feedstock processing to petrochemicals. A few studies have been done on Ga-based MFI catalysts. GaO-based catalysts were used for the Naphtha, LPG and ethane hydrocarbon conversion or aromatisation reactions. Used cooking oil, are rarely used to produce bio-aromatics.

Reference can be made to CN108484346A, which discloses thermal catalytic cracking of edible waste oil in the presence of HZSM-5 molecular sieve catalyst at a high temperature of 300-600° C. and 0.01~10.0 MPa pressure. The process took place in a fixed bed continuous reactor that helps in the continual production of aromatic hydrocarbons. The reaction pressure was varied between 0.01-10.0 MPa in the fluidised bed reactor, deviating from the invention disclosed. In the present disclosure, a fixed bed downflow reactor is used which can significantly process UCO in a single reactor with varying catalyst formulation and process conditions.

Reference can be made to CN110694673A, which discloses cracking edible waste oil comprising triglyceride, and free fatty acid. The metal oxide supported hierarchical pore HZSM-5 catalyst at 300-1000° C. temperature and 0.01-5.0 MPa pressure (WHSV 0.01 $h^{-1}$ to 10.0 $h^{-1}$) gives a 70% hydrocarbon yield. The major drawback of this process is that it is limited to UCO, and the possibility of extending it, is not mentioned. Additionally, the process gave high hydrocarbon but did not disclose the aromatic amount in the product steam.

Reference can be made to WO2015134570A1 for converting at least one fatty acid into branched, cyclic, aromatic, and cracked hydrocarbons. The fatty acid contains one free fatty acid (FFA) molecule obtained from plant oils; animal fats, algae oils; waste vegetable oils; and oils from heterotrophic microbes. The process occurs at 200-325° C. and 20 bar pressure. The major drawback of the process is that the reaction occurred at high pressure, and a single fatty acid was used for the process. Moreover, the aromatics yield is not disclosed at all.

Reference can be made to CN101684056A for converting animal and plant/vegetable oils into arene Hydrocarbons. The process uses a zeolite catalyst at (300-650° C.) temperature and 0.1-3.0 MPa pressure to give 69.39% aromatics selectivity. The reaction was carried out over a metal-supported ZSM-5 or Y-zeolite catalyst at 640° C., 1.0 MPa pressure. The drawback of the process is that (a) high pressure and (b) high temperature was applied to get the desired aromatics, which is less selective than the present invention.

Reference can be made to JP2015189712A for converting alcohol, aldehyde, ketone or carboxylic acid esters, a constituent of vegetable oil and fat, into aromatics hydrocarbons. The alcohols selected from a group consisting of 2-octanol, 1-octanol, 1-heptanol, 1-hexanol and 1-pentanol and the process take place over a Zn-ZSM-5 catalyst at (350-650° C.) temperature and 0 kPaG to 300 kPaG pressure to give 45-75% aromatics yield. The major drawback of this reaction is that (a) reference alcohol, ketone, esters was used and (b) 500° C. was optimised to have 45-75% aromatics yield.

Reference can be made to US20180010052A1 for hydrocracking of renewable feedstock (plant, animal or algae oil, lipids, glycerides and fatty acids) into hydrocarbons ranging between C1-C24 carbon number, comprising of n-paraffins, isoparaffins, cyclo paraffins, naphthenes, and aromatics and polynuclear aromatics. The process takes place using sulphide-based catalyst at (250-500° C.) temperature and 10 to 150 atm pressure. The major drawback of the reaction is that (a) it occurs in hydrogen environment (b) at high pressure and (c) give predominantly kerosene and diesel range hydrocarbons where aromatic is a side product.

Reference can be made to WO2000021661A1 for converting a hydrocarbon feed-stream into aromatics hydrocarbons using faujasitic and promoted FCC catalyst. The invention has FCC based catalyst having different promoter Fe, Ga, Zn, B, Cr, Ni or Co were used.

Reference can be made to SU1714836A1 for aromatisation of C3-C12 Petrochemicals hydrocarbons. The process takes place using ZSM-5/ZSM-11 catalyst having 1.0-5.0 zinc and/or gallium with promoter: 0.05-0.8 sulfur. The yield of aromatic hydrocarbons in the presence of given catalyst does not substantially decrease up to 100 hours. The invention has discussed the metal sulphide based ZSM-5/ZSM-11 catalyst.

Reference can be made to RU2652986C1 for converting vegetable oils into alkane-aromatics or gasoline hydrocarbons. The catalyst comprises of Pd and Ag over $Al_2O_3$ and zeolite MFI support and the reaction was carried out at 280-400° C., 10-50 atm of hydrogen pressure. The major drawback of the reaction is that it occurred at high pressure and requires presence of hydrogen, moreover a precious metal has been used as a catalyst which is highly expensive.

Reference can be made to US20070007176A1 for FCC catalytic cracking of vegetable oils into diesel. It shows excellent efficiency for obtaining highly pure products but does not yield glycerine, and one by-product of the transesterification process. The invention was for a diesel range hydrocarbon form vegetable oils.

Reference can be made to CN101314748A for catalytic cracking of vegetable oils/animal oil into large number of products including low-carbon olefin, gasoline, diesel oil and heavy oil. The method was highly applicable for olefin production C2-C4 using MFI and beta zeolite catalyst in a FFC reactor. The invention is different as (a) olefin is the major product, and (b) production of aromatics is not being reported.

Reference can be made to ID201202918A for hydrotreatment of renewable source using modified zeolite into hydro isomeric product. The invention discusses implementation in a modified zeolite.

Reference can be made to EP2781497A1 for hydro-dehydrogenation of renewable resources (paraffinic feedstock) using Fischer-Tropsch process. The invention discusses hydro-dehydrogenation using zeolite Nu-10 and ZSM-48 catalyst at a temperature of 150-500° C., pressure of 0.1-15 MPa and an hourly space velocity of 0.1-10 $h^{-1}$ and in presence of hydrogen. The process is entirely different as it focusses on middle distillate not in aromatics.

Thus, from the aforesaid documents, it can be observed that there is no prior art related to a single step production of aromatic hydrocarbons mainly comprising BTEX at low temperature with a single catalyst. Hence, there is a dire need in the art to develop a single-step process utilizing an efficient metal-based catalyst for the production of aromatics through sustainable routes.

OBJECTS FOR THE INVENTION

The main objective of the present invention is therefore to provide a catalytic process to produce aromatic hydrocarbon from used cooking oil.

Another objective of the present invention is to provide a noble metal free bi-metallic catalyst comprising zinc (Zn), and a second metal, comprising at least one from cobalt (Co), gallium (Ga), chromium (Cr), and promoted with a third elements from cerium (Ce) or boron (B).

Yet another objective of the present invention is to provide a process, which selectively gives aromatic (BTX) via aromatisation, with an 89% conversion diluted with nitrogen in presence or absence of molecular hydrogen/steam.

Still another objective of the present invention is to provide a process and noble metal free catalyst for the production bio-BTX.

Yet another objective of the present invention is to provide a process which works continuously for more than 4 h without any major deactivation of the catalyst under continuous process to produce aromatic from UCO.

SUMMARY OF THE INVENTION

The present invention relates to a process for the conversion of used cooking oil into aromatics (BTEX) hydrocarbon as petrochemical building blocks. The present feed consists of $C_{16}$-$C_{18}$ free fatty acid molecules having a density of 0.91 g/cm$^3$ with a viscosity of 42.5 mm$^2$/s. The process provides an aromatic rich hydrocarbon from used cooking oil in the presence and absence of steam/hydrogen over supported polymetallic alumina-silicates zeolites. More particularly, the present invention relates to a low-temperature process where >70% liquid yield was obtained over a supported zeolite catalyst. Overall, the aromatic, rich product stream can be used for the production of BTEX via the existing refinery setup.

In an embodiment, the present invention provides a process for the preparation of aromatics hydrocarbon by aromatisation from used cooking oil using a polymetallic alumina-silicate zeolite catalyst comprising the steps of:
  (a) synthesizing the Zn—X-MFI catalyst by adding the nitrate/chloride salt or acids of elements selected from the group consisting of Zn, Co, Ga, Cr, Fe, Ce and B (Sigma-Aldrich, ≥99%) in CTAB dissolved in water heated at 70° C. to obtain a mixture, wherein the weight ratio of X to MFI is kept in the range of 3 to 6% and the weight ratio of Zn to MFI is kept in the range of 6 to 10%;
  (b) homogenizing the mixture obtained in step [a] and further heating to 50 to 80° C. under stirring for 1 h to obtain a homogenized mixture;
  (c) successively adding 1 to 10 wt. % of the nano porous MFI zeolite to the homogenized mixture obtained in step [b] under stirring for 12-16 h at a temperature of 50 to 80° C. to obtain a precipitate;
  (d) cooling the precipitate obtained in step [c] to room temperature naturally, followed by collecting and washing with ethanol and water several times to obtain a material;
  (e) calcining the material obtained in step [d] at 350 to 550° C. for 4-6 h in air to obtain the desired Zn—X-MFI catalyst;
  (f) aromatising the used cooking oil [UCO] in a fixed bed down-flow reactor with the catalyst obtained in step [e] in the absence or presence of 1-5% nitrogen or steam while maintaining the reactor at atmospheric pressure at a temperature in a range of 250-550° C. with a gas hourly space velocity (GHSV) in the range of 600-1800 $h^{-1}$ and liquid hour space velocity (LHSV) in the range of 1.5-2.5 $h^{-1}$ to obtain reaction products comprising aromatics, wherein X is selected from Co, Ga, Cr, Fe, Ce, B or combinations thereof.

In another embodiment, the present invention provides a process wherein the reaction products are predominated with aromatics (benzene, toluene and xylene), diaromatics and polyaromatics.

In still another embodiment, the present invention provides a process wherein the conversion of UCO to aromatics is in a range of 84-89%.

In still another embodiment, the present invention provides a process wherein the conversion of UCO to aromatics is in a mol range of 84-89%.

In yet another embodiment, the present invention provides a process wherein the selectivity towards aromatics is in a range of 87-91%.

These and other features, aspects, and advantages of the present subject matter will be better understood with reference to the following description. This summary is provided to introduce a selection of concepts in a simplified form. This summary is not intended to identify key features or essential features of the disclosed subject matter, nor is it intended to be used to limit the scope of the disclosed subject matter.

BRIEF DESCRIPTION OF THE ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

LIST OF ALL THE ABBREVIATIONS USED

Figure 1:
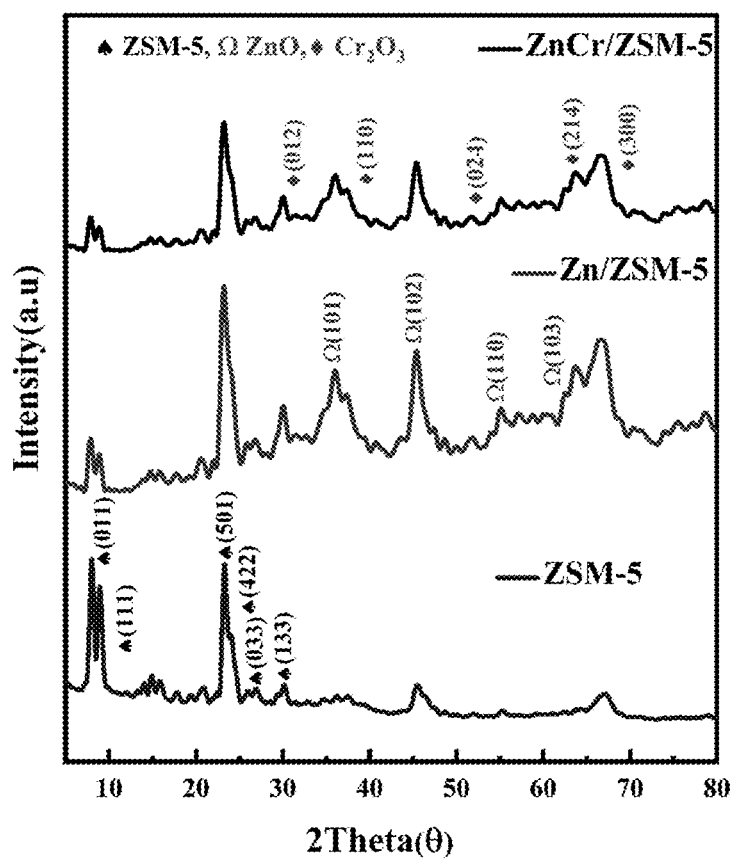
FIG. 1 represents X-ray Diffraction (XRD) pattern of the prepared catalyst, in accordance with an embodiment of the present disclosure.

| | |
|---|---|
| BTEX | Benzene, Toluene, Ethylbenzene, xylene |
| UCO | Used cooking oil |
| MFI | Zeolite Mobil type Five |
| Cr | Chromium |
| Zn | Zinc |
| Co | Cobalt |
| B | Boron |
| Ga | Gallium |
| Fe | Iron |
| CTAB | Cetyl trimethylammonium bromide |
| XRD | X - ray Diffraction |
| SEM | Scanning Electron Microscope |
| TEM | Transmission Electron Microscope |
| GHSV | Gas hourly space velocity |
| LHSV | Liquid hourly space velocity |

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "at least one" is used to mean one or more and thus includes individual components as well as mixtures/combinations.

The term "polymetallic alumina-silicate zeolite catalyst" refers to a catalyst comprising at least two elements selected from the group consisting of Zn, Co, Ga, Cr, Fe, Ce and B, impregnated on an alumina-silicate zeolite surface. In an aspect of the present disclosure, the catalyst comprises one, two or three elements independently selected from the group of Zn, Co, Ga, Cr, Fe, Ce and B.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, weight percentage in the range of 3-6% should be interpreted to include not only the explicitly recited limits of 3-6% but also to include sub-ranges, such as 3% to 3.9%, 4.1% to 5% and so forth, as well as individual amounts, including fractional amounts, within the specified ranges, such as 4.8%, 3.5% and 5.93%.

The present disclosure is not to be limited in scope by the specific embodiments described herein, which are intended for the purposes of exemplification only. Functionally equivalent products, compositions, formulations, and methods are clearly within the scope of the disclosure, as described herein.

As discussed in the background, there is a need in the art to develop a single step process for the production of aromatic hydrocarbons mainly comprising BTEX at low temperature with a single catalyst. Thus, in view of the drawbacks of various attempts made in the art, the present invention provides a process for converting used cooking oil (UCO) into aromatic (BTEX) rich hydrocarbons, which runs at an atmospheric pressure (in the absence of hydrogen) to achieve 88-91% aromatics selectivity at a temperature of 450° C., wherein the employed catalyst does not contain any noble metal and comprises zinc (Zn), with a second metal selected from a group comprising of cobalt (Co), gallium (Ga), chromium (Cr), iron (Fe) and third element from cerium (Ce), and boron (B), and wherein the catalyst can be prepared easily and is stable under the reaction condition; thereby leading to economical production of aromatics such as benzene, toluene and xylene.

The present invention provides a catalyst consisting of a transition metal, comprising zinc (Zn), and a second metal, comprising at least one selected from cobalt (Co), gallium (Ga), chromium (Cr), Iron (Fe) and/or a promoter element from cerium (Ce), and boron (B) on porous alumina-silicates zeolite, MFI etc. The amount of transition metal is kept in the range from 6 to 10 wt % based on the porous zeolite support, the amount of second metal is kept in the range from 3 to 6% and third element's composition is in the range from 1 to 3%. The catalyst is prepared by wetness impregnation method and calcined at different temperatures. The process is performed at atmospheric pressure, at a temperature range of 350 to 450° C. with a gas hourly space velocity (GHSV) in the range of 1200-1800 $h^{-1}$ and LHSV 1.5-3.5 $h^{-1}$. The catalyst is found stable for a period of 4 h time-on-steam and recyclable up to 3 cycles.

In an aspect, the present invention provides a catalyst composition comprising:
(a) a porous alumina-silicates zeolite MFI as support;
(b) a transition zinc (Zn), wherein the amount of transition metal is kept between 6 to 10 wt % based on the porous zeolite support;
(c) a second metal selected from cobalt (Co), gallium (Ga), chromium (Cr), or iron (Fe) wherein amount of the second metal is kept between 3 to 6 wt % based on the catalyst support; and
(d) a promoter element from cerium (Ce), and boron (B) wherein amount of the third metal is kept between 1 to 3 wt % based on the catalyst support.

In another aspect, the present invention provides a catalyst composition, wherein the porous alumina-silicates zeolite catalyst useful for oil aromatisation for aromatics (BTX) production in a continuous downflow reactor at low temperature.

In still another aspect, the present invention provides a process for synthesis of a catalyst composition comprising the steps of:
(a) depositing the transition metal, Zn on the porous alumina-silicates zeolite support to obtain a catalyst precursor; or
(b) depositing the metalloids, Ga, and Co or Cr, Fe transition metal on the porous alumina-silicates zeolite support to obtain a catalyst precursor; or
(c) depositing the elements, Ce, and B on the porous alumina-silicates zeolite support to obtain a catalyst precursor; and
(d) exposing the catalyst precursor to calcination in an environment comprising air or nitrogen to obtain a catalyst, where step (a) and (b) comprises the alumina-silicates zeolite MFI, as catalyst support with a solution comprising salts of the metals.

In still another aspect, the present invention relates to the preparation of Zn-MFI catalyst as described above, for low temperature aromatic production from UCO, comprising the following steps:
(i) synthesizing zinc impregnated MFI using zinc precursor and CTAB dissolved in water to obtain a mixture;
(ii) homogenizing the mixture obtained in step [i] and further heating at a temperature in a range of 50 to 80° C. under stirring for 1 h to obtain a homogenized mixture;
(iii) successively adding nanoporous MFI zeolite (2-10 g) to 50 to 100 ml of the homogenized mixture obtained in step [ii] under stirring for 12-16 h at a temperature in a range of 50 to 80° C. to obtain a precipitate;
(iv) cooling the precipitate obtained in step [iii] to room temperature naturally, followed by collecting and washing with ethanol and water several times to obtain a material;
(v) calcining the material obtained in step [iii] at 350 to 550° C. for 4-6 h in air to obtain solid Zn-MFI catalyst;
(vi) aromatising the UCO in a fixed bed down-flow reactor with the Zn-MFI obtained in step [v] using $N_2$ as a carrier gas to get aromatics, while maintaining the process pressure at 1 atmosphere and the reaction temperature in the range of 250 to 550° C., the gas hourly space velocity (GHSV in $h^{-1}$) in the range of (600 $h^{-1}$ to 1800 $h^{-1}$) and LHSV-1.5-3.5 $h^{-1}$ to obtain reaction products comprising aromatics wherein the oil conversion (mol %) is 82-85% and selectivity towards aromatics is 82-84%.

In yet another aspect, the present invention relates to the synthesis of Zn—Fe-MFI catalyst as described above, for low temperature aromatic production from UCO comprising the following steps:
(a) synthesizing Zn—Fe-MFI catalyst by adding iron nitrate (Sigma-Aldrich, ≥99%) as source of Fe to CTAB dissolved in water heated at 70° C. to obtain a mixture, wherein the weight ratio of Fe to MFI is kept in a range of 3 to 6% and the weight ratio of Zn precursor to MFI is kept in a range of 6 to 10%;
(b) homogenizing the mixture obtained in step [a] and further heating to 50 to 80° C. under stirring for 1 h to obtain a homogenized mixture;
(c) successively adding measured amount of nanoporous MFI zeolite (2-10 g) to 50 to 100 ml of the homogenized mixture obtained in step [b] under stirring for 12-16 h at a temperature of 50 to 80 degree C. to obtain a precipitate;
(d) cooling the precipitate obtained in step [c] to room temperature naturally, followed by collecting and washing with ethanol and water several times to obtain a material;
(e) calcining the material obtained in step [d] at 350 to 550° C. for 4-6 h in air to obtain the Zn—Fe-MFI catalyst;
(f) aromatising the UCO in a fixed bed down-flow reactor with the Zn—Fe-MFI obtained in step [e] using $N_2$ as a carrier gas, while maintaining the process pressure at 1 atmosphere, reaction temperature in the range of 250 to 550° C.; gas hourly space velocity (GHSV) in the range of (600 $h^{-1}$ to 1800 $h^{-1}$) and LHSV-1.5-3.5 $h^{-1}$ to obtain reaction products comprising aromatics wherein the oil conversion (mol %) is 84-86% and selectivity towards aromatics is 83-85%.

In still another aspect, the present invention relates to the synthesis of Zn—Ga-MFI catalyst for low-temperature aromatic production from UCO, comprising the following steps:
- (i) synthesizing Zn—Ga-MFI catalyst by adding gallium nitrate (Sigma-Aldrich, ≥99%) as source of Ga and CTAB dissolved in water heated at 70° C. to obtain a mixture, wherein the weight ratio of Ga to MFI is kept in the range of 3 to 6% and the weight ratio of Zn to MFI is kept in the range of 6 to 10%;
- (ii) homogenizing the mixture obtained in step [i] and further heating to 50 to 80° C. under stirring for 1 h to obtain a homogenized mixture;
- (iii) successively adding measured amount of nano porous MFI zeolite (2-10 gm) to 50 to 100 of the homogenized mixture obtained in step [ii] under stirring for 12-16 h at a temperature of 50 to 80° C. to obtain a precipitate;
- (iv) cooling the precipitate obtained in step [iii] to room temperature naturally, followed by collecting and washing with ethanol and water several times to obtain a material;
- (v) calcining the materials obtained in step [iv] at 350 to 550° C. for 4-6 h in air to get Zn—Ga-MFI catalyst;
- (vi) aromatising the UCO in a fixed bed down-flow reactor with the Zn—Ga-MFI obtained in step [v] in a fixed bed down-flow reactor using $N_2$ as a carrier gas to get aromatics, wherein the process pressure is kept at 1 atmosphere, the reaction temperature is in the range of 250 to 550° C., the gas hourly space velocity (GHSV) is preferably in the range of (600 $h^{-1}$ to 1800 $h^{-1}$) and LHSV-1.5-3.5 $h^{-1}$ to obtain reaction products comprising aromatics wherein the oil conversion (mol %) is 85-87% and selectivity towards aromatics is 87-89%.

In yet another aspect, the present invention relates to the synthesis of Zn—Cr-MFI catalyst for aromatisation of UCO to produce aromatics (BTX) involving the following steps:
- (a) synthesizing the Zn—Cr-MFI catalyst by adding Chromium nitrate (Sigma-Aldrich, ≥99%) as source of Cr to CTAB dissolved in water heated at 70° C. to obtain a mixture, wherein the weight ratio of Cr to MFI is kept in the range of 3 to 6% and the weight ratio of Zn to MFI is kept in the range of 6 to 10%;
- (b) homogenizing the mixture obtained in step [a] and further heating to 50 to 80° C. under stirring for 1 h to obtain a homogenized mixture;
- (c) successively adding measured amount of nano porous MFI zeolite (2-10 gm) to 50 to 100 ml of the homogenized mixture obtained in step [b] under stirring for 12-16 h at a temperature of 50 to 80° C. to obtain a precipitate;
- (d) cooling the precipitate obtained in step [c] to room temperature naturally, followed by collecting and washing with ethanol and water several times to obtain a material;
- (e) calcining the material obtained in step [d] at 350 to 550° C. for 4-6 h in air to get Zn—Cr-MFI; and
- (f) aromatising the UCO in a fixed bed down-flow reactor with the Zn—Cr-MFI obtained in step [e] in a fixed bed down-flow reactor using $N_2$ as a carrier gas to get aromatics, wherein the process pressure is kept at 1 atmosphere, the reaction temperature is in the range of 250 to 550° C.; the gas hourly space velocity (GHSV) is in the range of (600 $h^{-1}$ to 1800 $h^{-1}$) and LHSV-1.5-3.5 $h^{-1}$ to obtain reaction products comprising aromatics wherein the oil conversion (mol %) is 86-89% and selectivity towards aromatics is 87-91%.

In still another aspect, the present invention relates to the synthesis of Zn—Co-MFI catalyst for the aromatisation of UCO to produce aromatics (BTX) comprising the following steps:
- (i) synthesizing the Zn—Co-MFI catalyst using cobalt nitrate (Sigma-Aldrich, ≥99%) as source of Co and CTAB dissolved in water heated at 70° C. to obtain a mixture, wherein the weight ratio of Co to MFI is kept in the range of 3 to 6%, and the weight ratio of Zn to MFI is kept in the range of 6 to 10%;
- (ii) homogenizing the mixture obtained in step [i] and further heating to 50 to 80° C. under stirring for 1 h to obtain a homogenized mixture;
- (iii) successively adding measured amount of nano porous MFI zeolite (2-10 gm) to 50 to 100 ml of the homogenized mixture obtained in step [ii] under stirring for 12-16 h at a temperature of 50 to 80° C. to obtain a precipitate;
- (iv) cooling the precipitate obtained in step [iii] to room temperature naturally, followed by collecting and washing with ethanol and water several times to obtain a material;
- (v) calcining the materials obtained in step [iv] at 350 to 550° C. for 4-6 h in air to get Zn—Co-MFI;
- (vi) aromatising the UCO in a fixed bed down-flow reactor with the Zn—Co-MFI obtained in step [v] in a fixed bed down-flow reactor using $N_2$ as a carrier gas to get aromatics, wherein the process pressure is kept at 1 atmosphere, the reaction temperature is in the range of 250 to 550° C.; the gas hourly space velocity (GHSV) is in the range of (600 $h^{-1}$ to 1800 $h^{-1}$) and LHSV-1.5-3.5 $h^{-1}$ to obtain reaction products comprising aromatics wherein the oil conversion (mol %) is 87-89% and selectivity towards aromatics is 87-91%.

In a further aspect, the present invention relates to the synthesis of Zn—Cr—B-MFI catalyst for the aromatisation of UCO to produce aromatics (BTX) wherein the steps comprising:
- (a) synthesizing the Zn—Cr—B-MFI catalyst using Boric acid and Chromium nitrate (Sigma-Aldrich, ≥99%) as source of B and Cr and CTAB dissolved in water heated at 70° C. to obtain a mixture, weight the weight ratio of Cr to MFI is kept in the range of 3 to 6%, the weight ratio of Zn to MFI is kept in the range of 6 to 10% and the weight ratio of boron to MFI is kept in the range of 1 to 3%;
- (b) homogenizing the mixture obtained in step [a] and further heating to 50 to 80° C. under stirring for 1 h to obtain a homogenized mixture;
- (c) successively adding measured amount of nano porous MFI zeolite (2-10 gm) to 50 to 100 ml the homogenized mixture obtained in step [b] under stirring for 12-16 h at a temperature of 70° C. to obtain a precipitate;
- (d) cooling the precipitate obtained in step [c] to room temperature naturally, followed by collecting and washing with ethanol and water several times to obtain a material;
- (e) calcining the materials obtained in step [d] at 350 to 550° C. for 4-6 h in air to get Zn—Cr—B-MFI;
- (f) aromatising the UCO in a fixed bed down-flow reactor with the Zn—Cr—B-MFI obtained in step [e] in a fixed bed down-flow reactor using $N_2$ as a carrier gas to get reaction products comprising aromatics, wherein the process pressure is kept at 1 atmosphere, the reaction temperature is in the range of 250 to 550° C.; the gas hourly space velocity (GHSV) is in the range of (600 $h^{-1}$ to 1800 $h^{-1}$) and LHSV-1.5-3.5 $h^{-1}$ to obtain aromatics wherein the oil conversion (mol %) is 87-89% and selectivity towards aromatics is 87-91%.

In an important aspect, the present invention relates to a process for the conversion of used cooking oil into aromatics (BTEX) hydrocarbon as petrochemical building blocks using the catalysts as described above. The process provides aromatic rich hydrocarbons from used cooking oil in the presence and absence of steam/hydrogen over supported polymetallic alumina-silicate zeolites. The catalyst contains no precious metal entities and may contain one metal from zinc (Zn), a second metal, comprising at least one from cobalt (Co), gallium (Ga), chromium (Cr), iron (Fe) and third elements from cerium (Ce), boron (B) supported on alumina-silicate zeolites. The present invention also relates to a catalyst excluding noble metals to produce aromatics in a continuous fixed-bed reactor system under atmospheric pressure. The process of the present invention can be executed at low-temperature to produce aromatic over alumina-silicate zeolites. The process provides used cooking oil conversion of 84-89% with selectivity towards aromatics in a range of 87-91%.

EXAMPLES

The following examples are given by way of illustration only and therefore should not be constructed to limit the scope of the present invention in any manner.

Example 1: Synthesis of Metal Doped Alumina-Silicates

All the catalysts were synthesised by template assisted wet-impregnation method. The support alumina-silicates were chosen to comprise one of, MFI type zeolite; as they offer different pore network, surface area, etc. Metals were impregnated on the above-mentioned support in predefined manner. The concentration of metals was decided based on the already available industrial catalysts.

Example 2: Synthesis of Zinc Impregnated Alumina-Silicate Zeolites (Zn-MFI)

Synthesis of Zn-MFI was carried out by template assisted wetness impregnation method. The amount of zinc impregnated on the surface was kept in between 6-10%. It was synthesised by taking 10% by weight of zinc salt and CTAB dissolved in sufficient amount of water. Keep homogenizing the mixture at 70° C. for 1 h, during stirring, 5 g of MFI zeolite was added slowly into the vessel containing 50 to 100 ml of the homogenate obtained. The whole solution was allowed to stir for some more time (12-16 h) to ensure the homogeneity of the mixture. The obtained precipitate was cooled to room temperature. Then the solution was filtered using grade 1, 2.5 m Whatman filter paper and washed with water and ethanol. Finally, the calcination of the material was carried out at 350 to 550° C. for 4 h in air with slow ramp rate. The XRD pattern is shown in FIG. 1, and the morphology of the catalysts can be found in FIGS. 2 & 3.

Example 3: Synthesis of Ga Impregnated Zn-MFI Zeolites (Zn—Ga-MFI)

Synthesis of Zn—Ga-MFI was carried out by template assisted wetness impregnation method. The amount of gallium impregnated on the surface was kept in between 3-6%. The above-mentioned zeolite was synthesised by adding 10% of zinc salt, 5% by weight of gallium and CTAB dissolved in sufficient amount of water to obtain a mixture. The mixture was kept for homogenizing at 50 to 80° C. for 1 h, to obtain a homogenized mixture. During stirring, 5 g of MFI zeolite was added slowly into a different vessel containing 50 to 100 ml of the homogenized mixture. The whole solution was allowed to stir for some more time to ensure the homogeneity of the mixture. The solution was kept in an oven for overnight at 50 to 80° C. to obtain a precipitate. Then the solution was filtered using grade 1, 2.5 µm Whatman filter paper and washed with water and ethanol to obtain a material. Finally, the calcination of the material was carried out at 350 to 550° C. for 4 h in air with slow ramp rate to obtain the Zn—Ga-MFI catalyst.

Example 4: Synthesis of Fe Impregnated Zn-MFI Zeolites (Zn—Fe-MFI)

Synthesis of Zn—Fe-MFI was carried out by the template-assisted wetness impregnation method. The amount of Fe doped on the surface was kept in between 4-6%. The above-mentioned zeolite was synthesised by taking 5% by weight of iron salt and CTAB dissolved in sufficient amount water to obtain a mixture. The mixture was kept for homogenizing at 50 to 80° C. for 1 h, to obtain a homogenized mixture. 5 g of MFI zeolite was added slowly into different vessel containing 50 to 100 ml of the homogenized mixture during stirring. The whole solution was allowed to stir for some more time (12-16 h) to ensure the homogeneity of the mixture and to obtain a precipitate. The obtained precipitate was cooled to room temperature. Then the solution was filtered using grade 1, 2.5 m Whatman filter paper and washed with water and ethanol to obtain a material. Finally, the calcination of the material was carried out at 350 to 550° C. for 4 h in air with slow ramp rate to obtain the Zn—Fe-MFI catalyst.

Example 5: Synthesis of Co Impregnated Zn-MFI Zeolites (Zn—Co-MFI)

Synthesis of Zn—Co-MFI was carried out by template assisted wetness impregnation method. The amount of Co doped on the surface was kept in between 3-6%. The above-mentioned zeolite was synthesised by adding 5% by weight of cobalt salt and CTAB dissolved in sufficient amount water. Keep homogenizing the mixture at 50 to 80° C. for 1 h, during stirring to obtain a homogenized mixture. 5 g of MFI zeolite was added slowly into different vessel containing 50 to 100 ml of the homogenized mixture obtained. The whole solution was allowed to stir for some more time (12-16 h) to ensure the homogeneity of the mixture and to obtain a precipitate. The obtained precipitate was cooled to room temperature. Then the solution was filtered using grade 1, 2.5 m Whatman filter paper and washed with water and ethanol to obtain a material. Finally, the calcination of the material was carried out at 350 to 600° C. for 4 h in air with slow ramp rate.

Example 6: Synthesis of Cr Impregnated Zn-MFI Zeolites (Zn—Cr-MFI)

Figure 2:
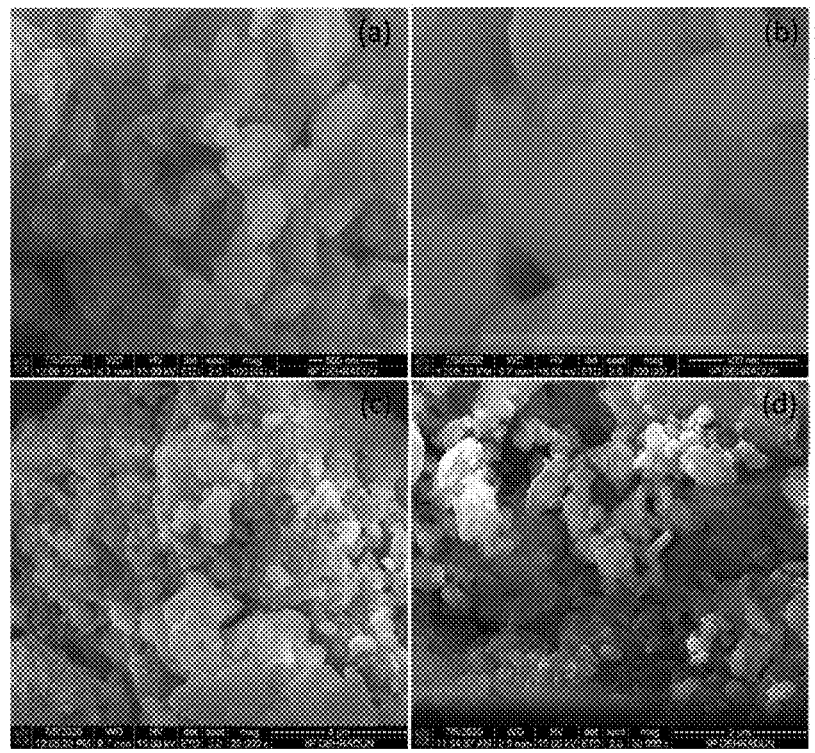
FIG. 2 represents Scanning Electron Microscope (SEM) images of the as prepared polymetallic alumina silicate catalyst, in accordance with an embodiment of the present disclosure.
Figure 3:
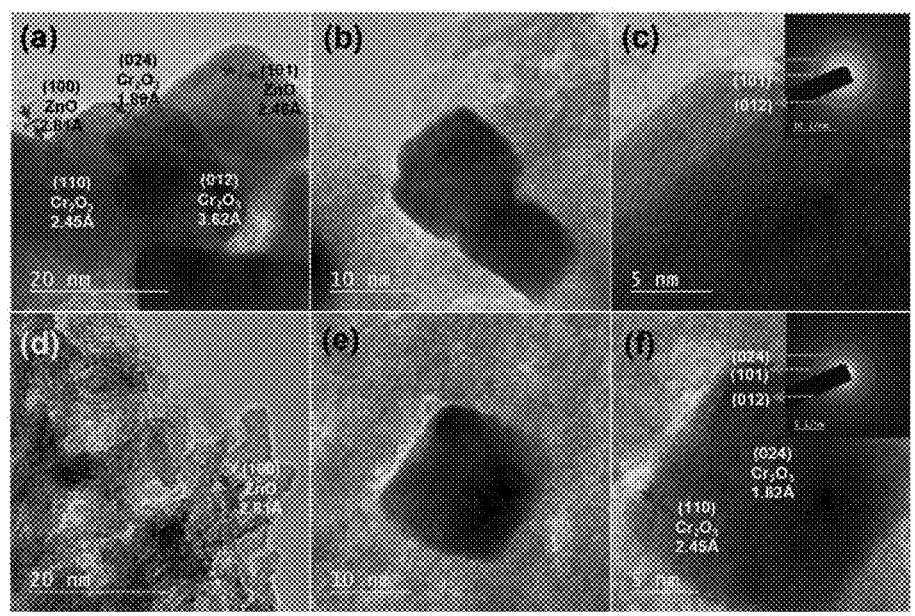
FIG. 3 represents Transmission Electron Microscope (TEM) images of the prepared catalyst, in accordance with an embodiment of the present disclosure.

Synthesis of Zn—Cr-MFI was carried out by template assisted wetness impregnation method. The amount of Cr was doped on the surface was maintained in between 3-6%. The above-mentioned zeolite was synthesised by adding 5% by weight of chromium salt to CTAB dissolved in sufficient amount water to obtain a mixture. The mixture was homogenized at 50 to 80° C. for 1 h, during stirring to obtain a homogenized mixture. 2-10 g of MFI zeolite was added slowly into different vessel containing 50 to 100 ml of the homogenized mixture. The whole solution was allowed to stir for some more time (12-16 h) to ensure the homogeneity of the mixture and to obtain a precipitate. The precipitate was cooled to room temperature. Then the solution was filtered using grade 1, 2.5 m Whatman filter paper and washed with water and ethanol to obtain a material. Finally, the calcination of the material was carried out at 350 to 550° C. for 4 h in air with slow ramp rate. The XRD pattern is shown in FIG. 1, and the morphology of the catalyst is shown in FIGS. 2 & 3.

Example 7: Synthesis of B Impregnated Zn—Cr-MFI Zeolites (Zn—Cr—B-MFI)

Synthesis of Zn—Cr—B-MFI was carried out by template assisted wetness impregnation method. The amount of B doped on the surface was kept in between 1-3%. The above-mentioned zeolite was synthesised by taking 3% by weight of boron salt, 5% by weight of chromium salt, 10% by weight of zinc salt and CTAB dissolved in sufficient amount water to obtain a mixture. The mixture was kept for homogenising at 50 to 80° C. for 1 h to obtain a homogenised mixture. 2-10 g of MFI zeolite was added slowly into different vessel containing 50 to 100 ml of the homogenized mixture during stirring. The whole solution was allowed to stir for some more time (12-16 h) to ensure the homogeneity of the mixture and to obtain a precipitate. The obtained precipitate was cooled to room temperature. Then the solution was filtered using grade 1, 2.5 m Whatman filter paper and washed with water and ethanol to obtain a material. Finally, the calcination of the material was carried out at 350 to 550° C. for 4 h in air with slow ramp rate.

Example 8

This example describes the vapour phase conversion/aromatisation of used cooking oil using all the synthesised nanocrystalline zeolites as catalysts.

The aromatisation of used cooking oil was carried out in a fixed bed downflow quartz reactor at atmospheric pressure. Typically, 1 g of catalyst was placed in between Silicon carbide with quartz wool plugged at the bottom of the 8 mm quartz reactor at 250-550° C. temperature. The gas hourly space velocity (GHSV) was varied between 600 $h^{-1}$ to 1800 $h^{-1}$, and liquid hour space velocity (LHSV) was varied from 1.5-3.5 $h^{-1}$.
Process Conditions:
  Catalyst: 1.0 g
  Zn-MFI catalyst
  Pressure: 1 atmosphere
  Total flow=15 ml/min (GHSV=900)
  Reaction time: 4 h

TABLE 1

| Catalyst | Temperature (° C.) | GHSV ($h^{-1}$) | LHSV ($h^{-1}$) | Conversion (mol %) * | Aromatics (BTX) Selectivity (mol %) † |
|---|---|---|---|---|---|
| Zn-MFI | 450 | 900 | 2 | 85 | 82 |

Example 9

This example describes the vapour phase conversion/aromatisation of used cooking oil using all the synthesised nanocrystalline zeolites as catalysts.

The aromatisation of used cooking oil was carried out in a fixed bed downflow quartz reactor at atmospheric pressure. Typically, 1 g of catalyst was placed between Silicon carbide with quartz wool plugged at the bottom of the 8 mm quartz reactor at 250-550° C. temperature.

The gas hourly space velocity (GHSV) was varied between 600 $h^{-1}$ to 1800 $h^{-1}$, and liquid hour space velocity (LHSV) was varied from 1.5-3.5 $h^{-1}$
Process Conditions:
  Catalyst: 1.0 g
  Zn—Cr-MFI catalyst
  Pressure: 1 atmosphere
  Total flow=15 ml/min (GHSV=900)
  Reaction time: 4 h

TABLE 2

| Catalyst | Temperature (° C.) | GHSV ($h^{-1}$) | LHSV ($h^{-1}$) | Conversion (mol %) * | Aromatics (BTX) Selectivity (mol %) † |
|---|---|---|---|---|---|
| Zn—Cr-MFI | 450 | 900 | 2 | 87.0 | 89.0 |

Example 10

This example describes the vapour phase conversion/aromatisation of used cooking oil using all the synthesised nanocrystalline zeolites as catalysts.

The aromatisation of used cooking oil was carried out in a fixed bed downflow quartz reactor at atmospheric pressure. Typically, 1 gm of catalyst was placed between Silicon carbide with quartz wool plugged at the bottom of the 8 mm quartz reactor at 250-550° C. temperature. The gas hourly space velocity (GHSV) was varied between 600 $h^{-1}$ to 1800 $h^{-1}$, and liquid hour space velocity (LHSV) was varied from 1.5-3.5 $h^{-1}$.
Process Conditions:
  Catalyst: 1.0 g
  Zn—Cr—B-MFI catalyst
  Pressure: 1 atmosphere
  Total flow=15 ml/min (GHSV=900)
  Reaction time: 4 h

TABLE 3

| Catalyst | Temperature (° C.) | GHSV ($h^{-1}$) | LHSV ($h^{-1}$) | Conversion (mol %) * | Aromatics (BTX) Selectivity (mol %) † |
|---|---|---|---|---|---|
| Zn—Cr—B-MFI | 450 | 900 | 2 | 89.0 | 91.0 |

Example 11

The example describes the effect of temperature on the used cooking oil aromatisation reaction. The product analysis is presented in Table-4.
Process Conditions:
  Catalyst: 1.0 g
  Zn—Cr-MFI as the catalyst
  Pressure: 1 atmosphere Total flow=15 ml/min (GHSV=900)
Reaction time: 4 h

TABLE 4

Effect of temperature on used cooking oil aromatisation

|  | Temperature (° C.) | Oil Conversion (mol %)* | Aromatic (BTX) Selectivity (mol %)† |
|---|---|---|---|
| Aromatisation of used cooking oil into aromatic | 250 | X − 32 | Y − 20 |
|  | 300 | X − 27 | Y − 15 |
|  | 400 | X − 25 | Y − 10 |
|  | 450 | X | Y |
|  | 500 | X + 5 | Y − 12 |
|  | 550 | X + 10 | Y − 17 |

*X − 89.0
†Y − 91.0

Example 12

Figure 4:
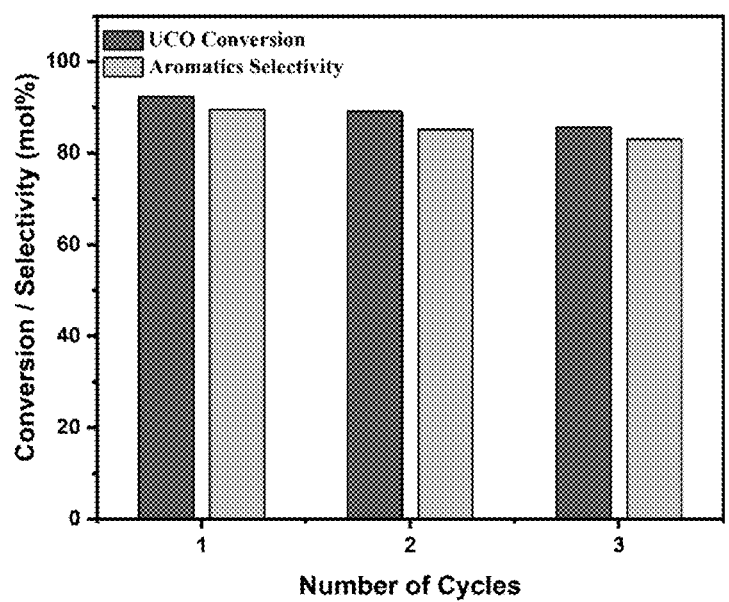
FIG. 4 represents the recyclability of polymetallic alumina silicate catalyst, in accordance with an embodiment of the present disclosure.

The example describes the recyclability of catalyst on the used cooking oil aromatisation reaction. The product analysis is presented in FIG. 4.

Process Conditions:
Catalyst: 1.0 g
Zn—Cr-MFI in the catalyst
Pressure: 1 atmosphere
Total flow=15 ml/min (GHSV=900)
Reaction time: 4 h

Advantages of the Invention

The present invention involves the production of aromatic hydrocarbons mainly comprising BTEX at a low temperature in a single step with a single catalyst.

The process provides good conversion and an excellent yield of light aromatics.

The process runs at an atmospheric pressure (in the absence of hydrogen) to achieve 87-91% of aromatics selectivity at a temperature of 450° C.

The employed catalyst does not contain any noble metal and comprises at least one metal form zinc (Zn), and a second metal, comprising at least one from cobalt (Co), gallium (Ga), chromium (Cr), Iron (Fe) and/or third elements from cerium (Ce), boron (B).

The catalyst can be prepared easily and stable under the reaction condition; therefore, very economical to produce aromatics (benzene, toluene, and xylene).

We claim:

1. A process for the preparation of aromatic hydrocarbons by aromatisation from used cooking oil using a polymetallic alumina-silicate zeolite catalyst comprising the steps of:
   a) synthesizing the Zn-X-MFI catalyst by adding nitrate/chloride salts or acids of elements selected from the group consisting of Zn, Co, Ga, Cr, Fe, Ce and B, to CTAB dissolved in water followed by heating at 70° C. to obtain a mixture, wherein the weight ratio of X to MFI is kept in a range of 3 to 6% and the weight ratio of Zn to MFI is kept in a range of 6 to 10%, wherein X is selected from Co, Ga, Cr, Fe, Ce, B, and combinations thereof;
   b) homogenizing the mixture obtained in step (a) followed by heating at a temperature in a range of 50 to 80° C. under stirring for 1 h to obtain a homogenized mixture;
   c) successively adding 1 to 10 wt % of a nano porous MFI zeolite to the homogenized mixture obtained in step [b] under stirring for 12-16 h at a temperature in a range of 50 to 80° C., to obtain a precipitate;
   d) cooling the precipitate obtained in step [c] to room temperature naturally, followed by collecting and washing with ethanol and water several times to obtain a material;
   e) calcining the material obtained in step [d] at 350 to 550° C. for 4-6 h in air to obtain the catalyst;
   f) aromatising a used cooking oil [UCO] in a fixed bed down-flow reactor with the Zn-X-MFI catalyst obtained in step [e] in the absence or presence of 1-5% nitrogen or steam while maintaining the reactor at atmospheric pressure at a temperature in a range of 250-550° C. with a gas hourly space velocity (GHSV) in a range of 600-1800 $h^{-1}$ and liquid hour space velocity (LHSV) in a range of 1.5-2.5 $h^{-1}$ to obtain reaction products comprising aromatics.

2. The process as claimed in claim 1, wherein the reaction products are predominated with aromatics (benzene, toluene and xylene), diaromatics and polyaromatics.

3. The process as claimed in claim 1, wherein the conversion of UCO to aromatics is in a mole range of 84-89%.

4. The process as claimed in claim 1, wherein the process has a selectivity towards aromatics in a range of 87-91%.

* * * * *